(12) United States Patent
Koros et al.

(10) Patent No.: US 7,314,331 B1
(45) Date of Patent: Jan. 1, 2008

(54) MULTI-POSITION LOCKING MECHANISMS FOR CLAMPING ASSEMBLIES

(76) Inventors: Tibor Koros, 610 Flinn Ave., Moorpark, CA (US) 93021; Gabriel Koros, 2054 Hathaway Ave., Thousand Oaks, CA (US) 91362

( * ) Notice: Subject to any disclaimer, the term of this patent is extended or adjusted under 35 U.S.C. 154(b) by 263 days.

(21) Appl. No.: 10/915,789

(22) Filed: Aug. 11, 2004

(51) Int. Cl.
*B25G 3/36* (2006.01)

(52) U.S. Cl. .................. 403/396; 403/385; 403/DIG. 4

(58) Field of Classification Search ................ 403/196, 403/374.5, 385, 389, 391, 395, 396, 398, 403/409.1, DIG. 4, DIG. 8, 177, 190, 191, 403/234–236, 399
See application file for complete search history.

(56) References Cited

U.S. PATENT DOCUMENTS

| 3,810,570 A | * | 5/1974 | Nagaoka ..................... 226/176 |
| 4,046,363 A | * | 9/1977 | Whitley ...................... 269/228 |
| 5,167,223 A | | 12/1992 | Koros et al. |
| 5,727,899 A | | 3/1998 | Dobrovolny |
| 5,792,046 A | | 8/1998 | Dobrovolny |
| 5,888,197 A | * | 3/1999 | Mulac et al. ............... 403/396 |
| 6,017,008 A | | 1/2000 | Farley |
| 6,277,069 B1 | | 8/2001 | Gray |
| 6,431,025 B1 | | 8/2002 | Koros et al. |
| 6,620,097 B1 | | 9/2003 | Bookwalter et al. |
| 6,736,775 B2 | | 5/2004 | Phillips |
| 6,739,223 B2 | * | 5/2004 | Wu ............................. 81/179 |

* cited by examiner

*Primary Examiner*—James M. Hewitt
*Assistant Examiner*—Victor MacArthur
(74) *Attorney, Agent, or Firm*—Fulwider Patton LLP

(57) ABSTRACT

A locking mechanism for a clamping assembly includes a roller locking mechanism, at least one clamping member and a shaft member for coupling the roller locking mechanism with the first clamping member. The roller mechanism includes a roller rotatably connected to a handle which contacts a bearing surface to place a compressive force on the first clamping member when the handle is actuated. Another locking mechanism includes a camming member having cam face with a sliding cam surface and a frictional cam surface adjacent to the sliding cam surface. The camming member produces a compressive force on the clamping member as the sliding cam surface contacts a bearing surface and increased static friction when the frictional cam surface contacts the bearing surface to help maintain the camming member in a locked position. Another locking mechanism includes a support frame, a camming member pivotally attached to the support frame, a clamping member and a shaft member for coupling the roller locking mechanism with the first clamping member, the shaft member including a sliding pin which remains in sliding engagement with the camming member.

8 Claims, 7 Drawing Sheets

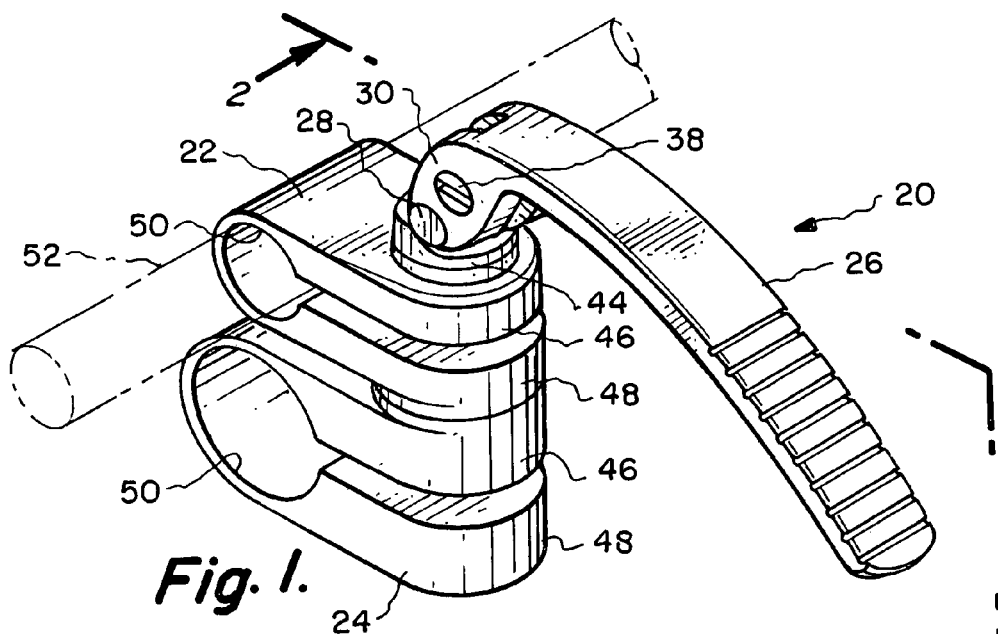
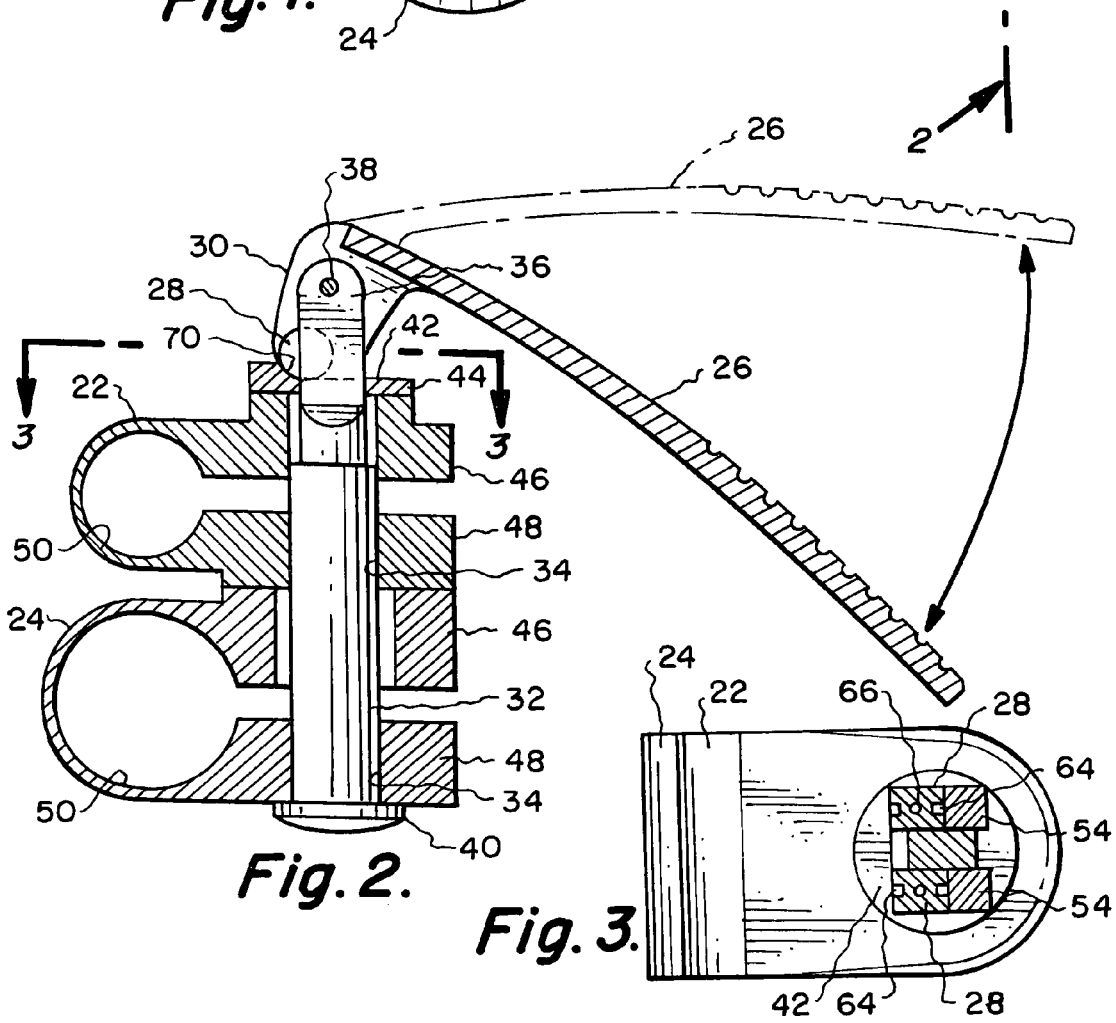

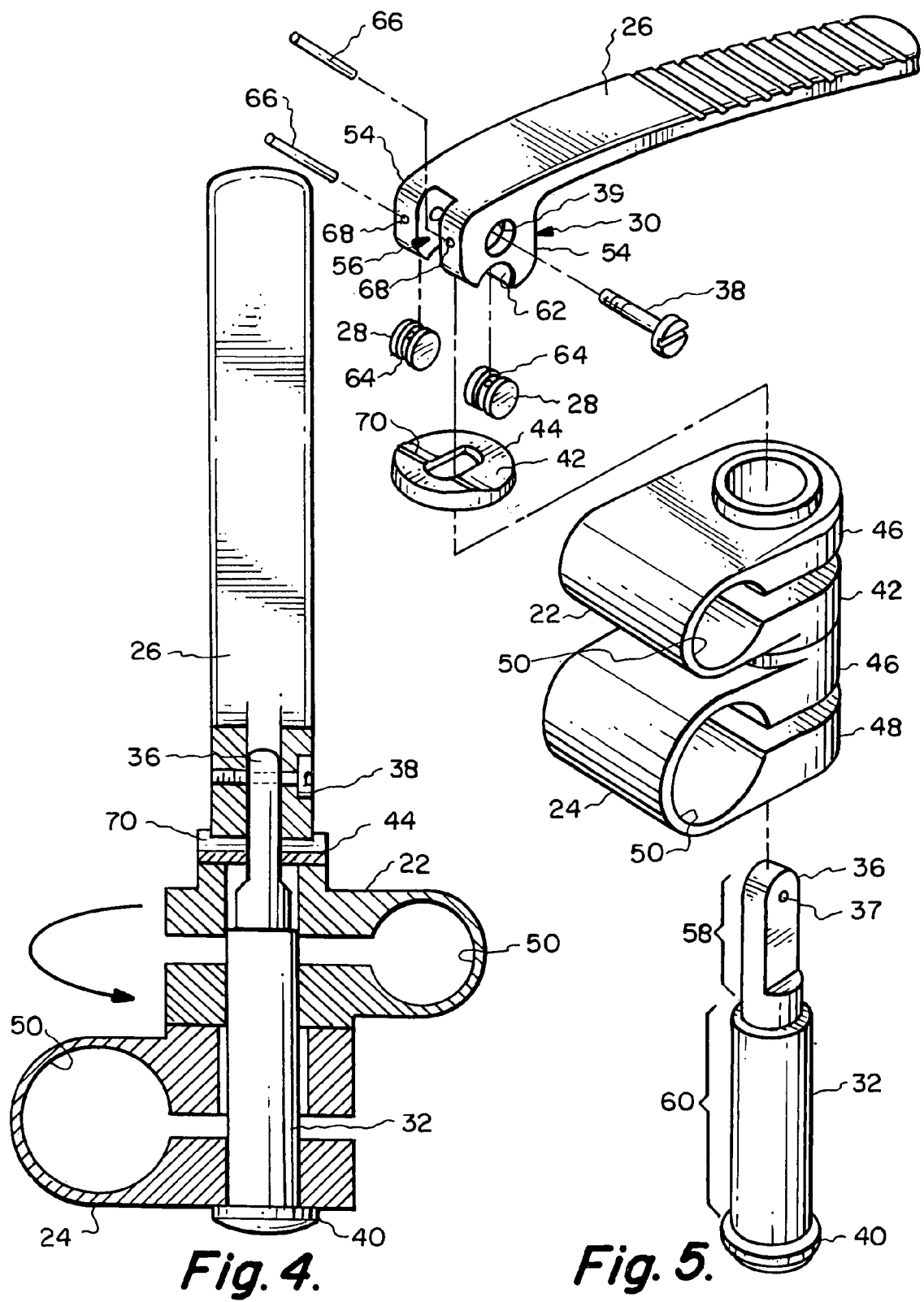

MULTI-POSITION LOCKING MECHANISMS FOR CLAMPING ASSEMBLIES

BACKGROUND OF THE INVENTION

The present invention generally relates to clamping devices for connecting discrete elements together, and more particularly, to locking mechanisms which can be used with clamping devices to provide the actuating force needed to move and maintain the clamping devices in a clamped and unclamped position. The present invention also is directed to locking mechanisms which can be associated with camming devices to increase the frictional contact between the cam surface and the contact surface to increase the ability of the camming member to be "locked" in a set position. While the present invention is described with particularity in use within the medical field, particularly to clamping devices used with surgical retraction systems, it should be appreciated that the present invention could be used in non-medical applications where the quick release of clamped elements is desired.

Various surgical retraction systems have been developed over the years for use in surgical operations which require access to internal organs and bone structures. Surgical retraction systems are used to hold back tissue and expose the area in which the surgical operation is to be performed. In many surgical retraction systems, a retractor clamp is utilized to hold the retractor blade used to engage and hold the patient's tissue. The retractor clamp is designed to be mounted on a retractor shaft or rail which is part of a support frame mounted to the operation room table above the patient. The support frame usually includes a number of rails erected above the surgical site which remain stationary throughout the surgical procedure. A number of retractor clamps with retractor blades can be placed along the support frame at appropriate positions to allow the retractor blades to retract the patient's tissue and expose the area for the surgical procedure. Due to factors such as the size and location of the surgical site, along with the variations in patient size, the desired exposure is not always directed to the center of the operation site, which many times require the blade retractors to be re-positioned, elevated or pushed down on the margins of the incision. Accordingly, it is important that the retractor clamp and retractor blade be designed for ease in repositioning into different angular positions as may be needed by the surgical staff in order to properly expose the surgical site for the surgery.

The retractor clamp usually includes an actuation means adapted to apply a compressive force to cause proper clamping engagement of the rod affixed to the retractor blade and the clamp to the rail support. The retractor clamp should be designed such that it is easy to manipulate the actuating means between clamped and unclamped positions and easily re-adjustable to achieve the desire tension necessary to hold back the tissue to expose the area to be surgically treated. It also is important that the retractor clamp itself does not create an obstruction to the surgical site.

Various types of clamping devices have been developed for retraction systems and include those disclosed in U.S. Pat. No. 5,727,899 (Dobrovolny); U.S. Pat. No. 5,792,046 (Dobrovolny); U.S. Pat. No. 5,888,197 (Mulac); U.S. Pat. No. 6,017,008 (Farley); and U.S. Pat. No. 6,277,069 (Gray). These patents generally relate to the basic concept of holding two rod sections in an adjustable and fixable angular relationship relative to one another when placed in a locked position. One of the rod sections is usually a retractor handle that has a retractor blade mounted at one end and is laterally adjustable to engage the tissue at the surgical site. The other rod section is usually the rail of the support frame which allows the retractor blade to be movably placed around the area of the surgical site. Different types of clamps are disclosed in these patents which are designed to engage these rod sections. Many of these devices include a universal joint mechanism which permits quick tightening of the retractor clamp for ease of movement on the rail system along with ease of movement of the retractor blade.

Several of these prior art surgical retraction systems utilize a camming member having a cam face or surface attached to a handle which allows the physician to move the handle in an upward or downward fashion to move the retractor clamp into the clamped or unclamped position. While a camming member is useful in producing the actuating force needed to move the various clamping devices in the clamped position, there is always a possibility that the camming surface can "slip" once placed in the clamped position which can diminish the force acting on the respective clamping devices. If the clamping force should decrease, it is possible for the rod section which holds the retractor blade, for example, to move especially since the retractor blade and retractor rod usually applies tension when retracting the patient's tissue. It should be appreciated that such a reduction in this clamping force is undesirable since the tension applied by the retractor blade to the retracted tissue can also be reduced which can cause the tissue to pull back to its original position.

Therefore, there is a need for the camming device to not only sufficiently develop the actuating or clamping force on the various clamping devices, but to maintain that force without slipping. When a camming surface is utilized, a loss or reduction of frictional contact between the camming surface and the contact surface can result in a loss in the clamping force. Additionally, the resiliency of the clamping device(s) often produces a counteracting force which acts on the camming member to basically urge the camming member back to an unclamped position, where no forces act on the camming member. Frictional contact helps to prevent the camming member from reverting back to the unclamped position; however, many of the prior art systems use an anti-galling washer to reduce friction as the cam face contacts the surface of the anti-galling washer. Reduction in the developed static friction, however, could cause the camming member to "loosen" or "slip" causing a reduction in the clamping force that keeps the components securely clamped together. Accordingly, it is important that the cam surface develop sufficient frictional contact when placed in a clamped or locked position to keep the retractor clamp stable during the entire surgical procedure.

What has been needed is an improved locking mechanism which provides the necessary actuating force to maintain the clamping member(s) in a clamped position without the fear that the locking mechanism will "slip" or "loosen" to cause a loss in the force needed to maintain the clamping member (s) in the clamped condition. Moreover, such a locking mechanism should be easy to deploy and include the ability to be rotated fully with respect to the clamping member(s) to allow greater flexibility in retractor blade placement at the surgical site. Additionally, such a locking mechanism should not obstruct access to the surgical site. The present invention satisfies these and other needs.

SUMMARY OF THE INVENTION

The present invention provides a multi-position locking mechanism which can be used with a clamping device(s) to create and maintain the necessary actuating or clamping force to maintain the device in a clamped position without substantial risk of slippage. The present invention is practical and particularly useful in the medical field as part of a surgical retraction apparatus used to provide exposure of an operative site. The present invention is sturdy, readily adjustable, easy to use and can be made from biocompatible material, such as stainless steel, which can be easily sterilized. While the present invention is particularly suitable for use in the medical field, it can have practical application in non-medical fields where quick release of clamped assemblies is desired.

In one aspect of the present invention, the multi-position locking mechanism includes a roller locking mechanism which is adapted to develop an actuating or compressive force that moves a component or assembly, such as a clamp, into a compressed or clamped position. The roller locking mechanism includes a roller which is rotatably attached to a handle and is adapted to contact a bearing surface that forms a portion of a composite clamping assembly. In one particular embodiment, a pair of clamping members can be coupled to the locking mechanism. The motion of the roller via the movement of the handle initially creates a compressive force on the particular component(s) coupled to the locking mechanism. The clamping member may have movable portions which are compressed by the action of the moving roller, which in turn, cause the clamping member to clamp the desired object. In the case when the present invention forms part of a surgical retraction system, the desired objects are usually the rod sections which form the support frame and the rods that hold the retractor blades.

The frictional force created by the roller is sufficiently large to maintain the handle in the closed, clamped position in part due to the increased friction derived from the attachment of the roller to the handle. The friction generate between the roller and it attachment point is small enough to allow the user to easily move the handle between clamped and unclamped positions, but is large enough to help hold the roller in frictional engagement with the bearing surface once the roller is placed in the clamped position. As a result, the roller and handle remain in the clamped position to maintain the clamping members tight, without fear that the mechanism will slip or loosen during usage. In one aspect of the present invention, the bearing surface is formed on a separate component, such as a washer, which includes an incline designed to contact the roller and increase the frictional force between the two components. Movement of the handle portion causes the roller to move into contact with the bearing surface which accordingly creates the compressive force which causes the portion of the clamping member (s) to assume the clamped position. The roller remains in frictional contact with the inclined washer keeping the clamping member(s) in the clamped position.

In another aspect of the present invention, the locking mechanism includes a camming member having cam face with a sliding cam surface and a frictional cam surface adjacent to the sliding cam surface. The camming member produces a compressive force on the clamping member as the sliding cam surface contacts a bearing surface and increased static friction when the frictional cam surface contacts the bearing surface to help maintain the camming member in a locked position. In one particular aspect, the friction surface is created by rotatably mounting a roller, such as the one described above, on the camming member. The frictional cam surface also can be created by placing a material having a higher coefficient of friction than the sliding cam surface directly onto the cam face. Other methods of producing a frictional cam surface include surface treatment which creates a roughened surface.

In yet another aspect of the present invention, the locking mechanism includes a support frame, a camming member pivotally attached to the support frame, a clamping member and a shaft member for coupling the roller locking mechanism with the first clamping member, the shaft member including a sliding pin which remains in sliding engagement with the camming member.

Other features and advantages of the present invention will become more apparent from the following detailed description of the invention when taken in conjunction with the accompanying exemplary drawings.

BRIEF DESCRIPTION OF THE DRAWINGS

FIG. 1 is a perspective view of one particular embodiment of a locking mechanism made in accordance with the present invention coupled to a pair of conventional clamping devices.

FIG. 2 is a cross-sectional side view of the composite device depicted in FIG. 1 taken along lines 2-2 which shows the contact between the roller and inclined washer when the locking mechanism is placed in the locked or clamped position.

FIG. 3 is a partial cross-sectional view of the composite device depicted in FIG. 1 taken along lines 3-3 which shows the roller member housed within the recessed formed in the handle portion of the locking mechanism.

FIG. 4 is a side elevational view, partially in cross-section, of the composite device depicted in FIG. 1 which shows the freedom of rotation between the various components.

FIG. 5 is an exploded perspective view of the components which form the composite device depicted in FIG. 1.

DETAILED DESCRIPTION OF THE PREFERRED EMBODIMENTS

Figure 6:
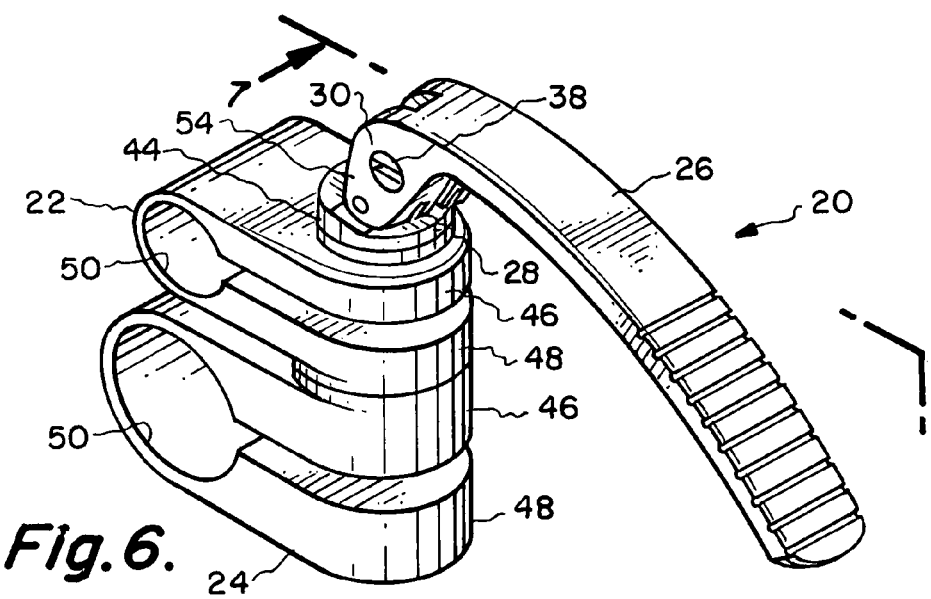
FIG. 6 is a perspective view of another particular embodiment of a locking mechanism made in accordance with the present invention coupled to a pair of conventional clamping devices.
Figure 7:
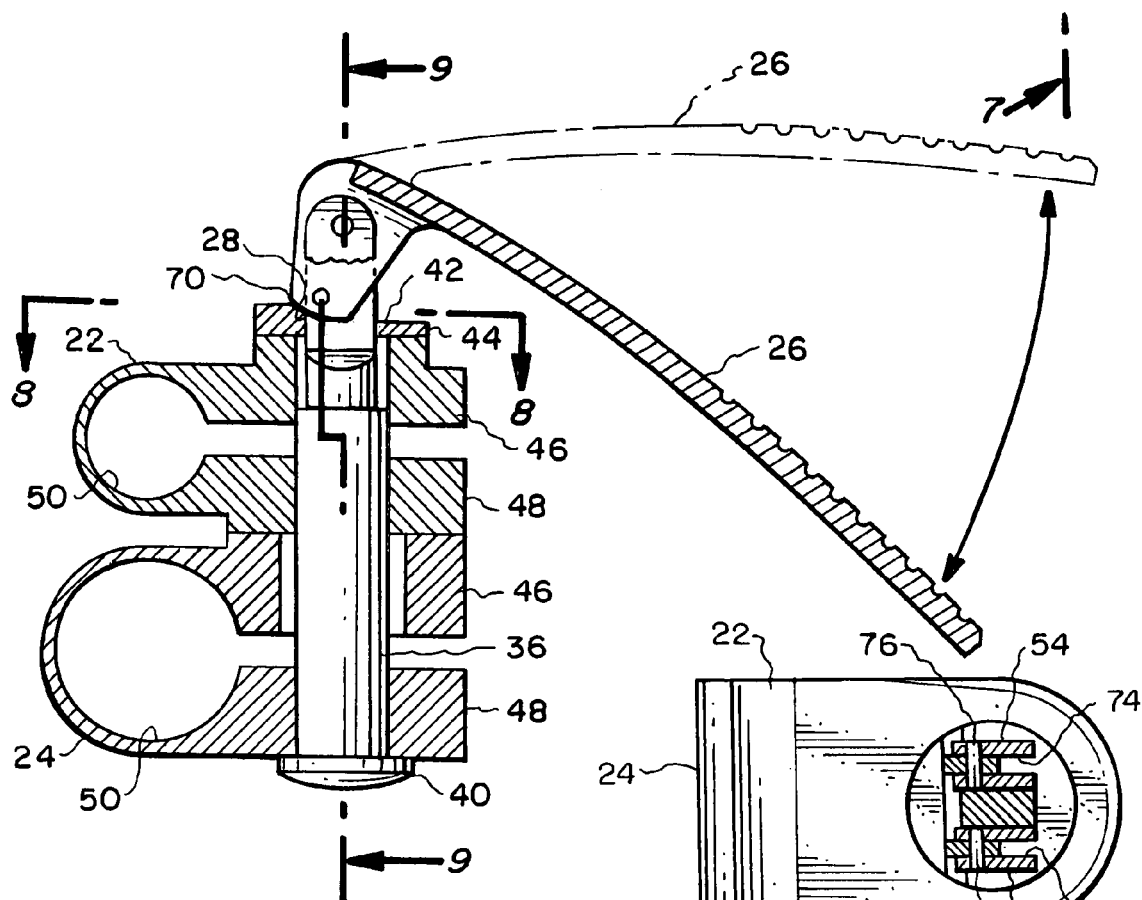
FIG. 7 is a cross-sectional side view of the composite device depicted in FIG. 6 taken along lines 7-7 which shows the contact between the roller and inclined washer when the locking mechanism is placed in the locked or clamped position.
Figure 8:
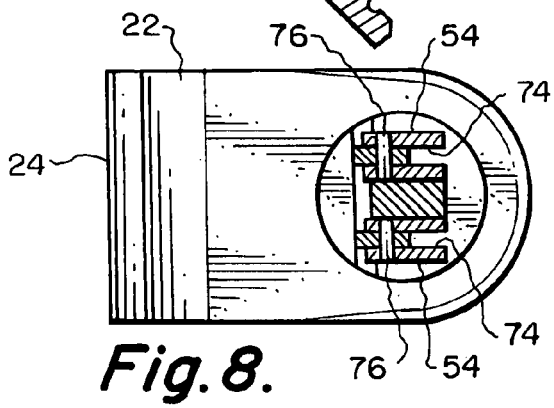
FIG. 8 is a partial cross-sectional view of the composite device depicted in FIG. 6 taken along lines 8-8 which shows the roller member housed within the recessed formed in the handle portion of the locking mechanism.
Figure 9:
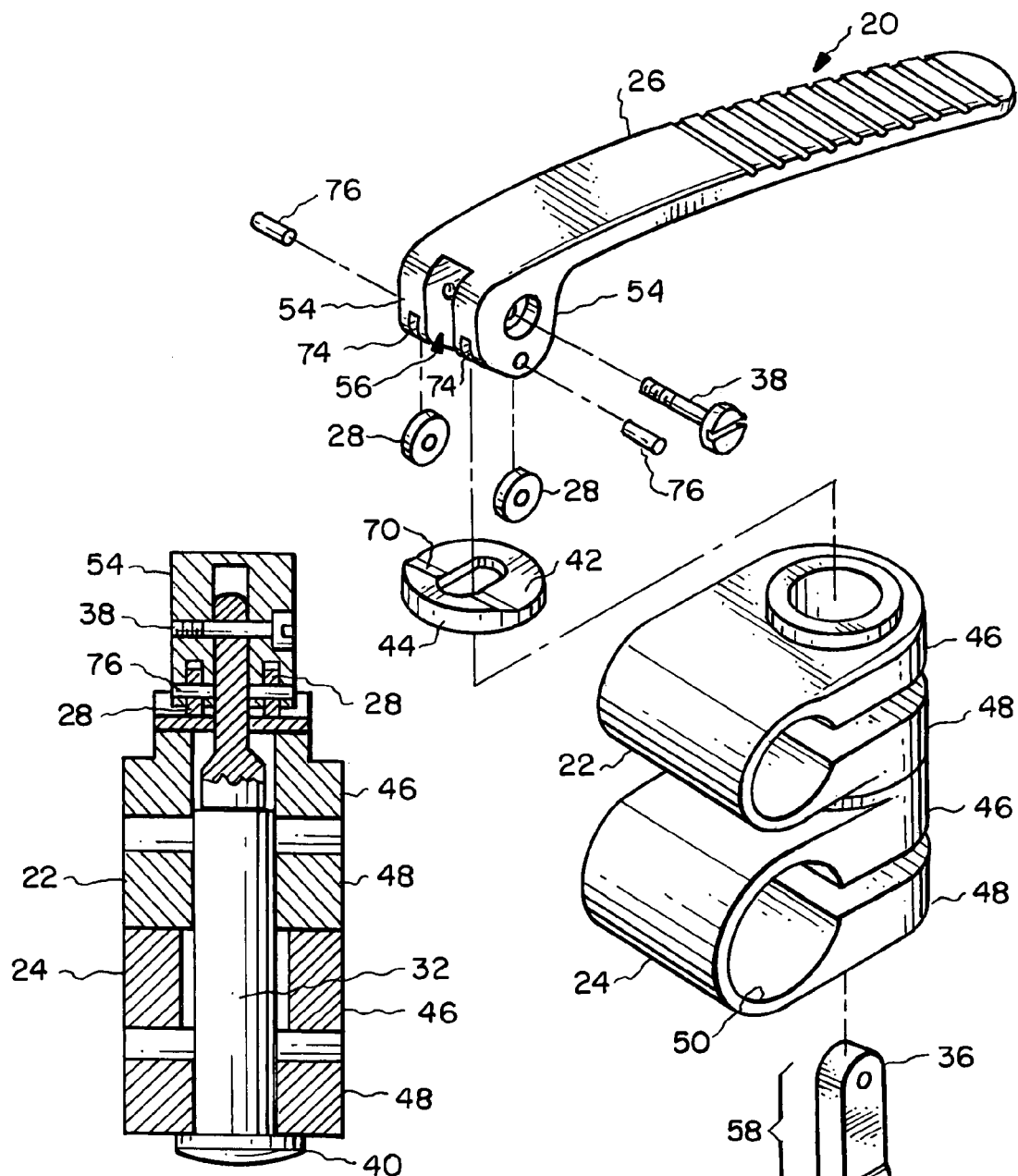
FIG. 9 is a side cross-sectional view of the composite device depicted in FIG. 6 taken along lines 9-9.

In one aspect, the present invention relates to locking mechanisms which can be used to deliver an actuating force that moves and locks, for example, a clamping device(s) between its clamped and unclamped positions. For the sake of illustration, the following exemplary embodiments of the invention are directed to clamping devices used in a surgical retraction system, although it should be understood that the present invention is applicable to other medical device applications, as well as non-medical applications.

Referring now to FIGS. 1-5, one particular embodiment of a multi-position locking mechanism 20 is shown. The locking mechanism 20 is used to impart an actuating or compressive force on a first clamping member 22 and a second clamping member 24 which are coupled to the locking mechanism 20. The combination of the locking mechanism 20 and the first clamping member 22 and second clamping member 24 creates a composite retractor clamp which is capable of being utilized, for example, in a surgical retraction system.

Referring specifically to FIG. 2, the locking mechanism 20 includes a handle 26 which can be manipulated by the user in an up and down position to place the first clamping member 22 and second clamping member 24 in a clamped or unclamped position. The upper position of the handle in FIG. 2 usually represents the unclamped position while the lower position of the handle in FIG. 2 usually denotes the clamped position. The handle 26 is usually placed in this downward clamped position to keep the handle free from contact during the operation.

The handle 26 includes the wheel or roller 28 which is rotatably attached to the head portion 30 of the handle 26. The head portion 30 of the handle 26 is pivotally connected to a shaft 32 which extends through openings 34 extending through the first clamping member 22 and second clamping member 24. One end 36 of the shaft 32 includes a bore 37 through which a screw pin 38 extends. The screw pin 38, in turn, extends through a bore 39 located in the head portion 30 of the handle 26 to allow the handle 26 to pivot about the axis defined by the screw pin 38. The other end of the shaft 32 has a stop 40 which contacts the second clamping member 24. In use, the handle 26 is designed to create an actuating or compressive force on the first clamping member 22 and second clamping member 24 via the pivoting action of the handle 26 as the roller 28 contacts a bearing surface 42. As the handle is moved in a downward position, the roller 28 creates the force which urges the first and second clamping members 22 and 24 together. This bearing surface 42 can be formed on the clamping member 24 itself, or it can be formed on a washer 44 or similar component which contacts the clamping member.

As can be best seen in FIGS. 1 and 2, each of the clamping members 22 and 24 includes a pair of leg portions 46 and 48 which are designed to move towards each other by the action of the locking mechanism 20. Each of the first and second clamping members 22 and 24 also includes an opening 50 designed to receive and clamp therein the desired object. As is shown in FIG. 1, the opening 50 of the first clamping member 22 shows in phantom a rod section 52 which is to be clamped therein. The movement of the leg portions 46 and 48 in turn imparts a compressive force on the object retained in the opening 50, thus clamping it in place. The rod section 52 can be, for example, the rod which is attached to the retractor blade of the surgical retraction system. Similarly, the opening of the second clamping member 42 can clamp therein, for example, a rail section which is part of the frame support mounted to the surgical table.

It should be appreciated that the first and second clamping members 22 and 24 shown in the preferred embodiments are typical of the many different types of clamping devices which can be utilized with any of the embodiments of the locking mechanisms of the present invention. Those skilled in the art will recognize that other types of clamps such as those shown in U.S. Pat. No. 5,888,197 (Mulac), U.S. Pat. No. 6,736,775 (Philips), U.S. Pat. No. 6,277,069 (Gray) and U.S. Pat. No. 6,017,008 (Farley), show different types of clamps which can be used with the present invention. Additionally, while the openings 50 on the clamping members 22 an 24 are shown as being circular, it should be appreciated that other shapes could be utilized for the clamp openings as well. For example, bars having rectangular or square cross sectional shapes, along with any one of a number of different shapes could be incorporated into the clamping member without departing from the spirit and scope of the present invention. Additionally, while two clamping members 22 and 24 are shown in this particular embodiment, it should be appreciated that the locking mechanism 20 could also be used with just a single clamp or it could be used with more than two clamps, depending upon the particular application. The number of different combinations of clamps and related accessories which can be utilized with the present invention is virtually endless.

Referring specifically now to FIGS. 1, 3 and 5, the roller 28 which is rotatably connected to the head portion 30 of the handle 26 is shown in greater detail. As can be seen best in FIG. 5, the head 30 of the handle 26 actually forms a pair of stationary jaws 54 which are substantially similarly sized and shaped in construction. A gap 56 is formed between the pair of stationary jaws 54 to allow the end 36 of the shaft 32 to be pivotally mounted to the handle 26. As can be seen in FIG. 5, the shaft 32 includes a formed section 58 at the end 36 which is machined to a particular shape to allow it to extend into the gap 56 of the handle for pivotal attachment. The main body of the shaft 32 can be substantially cylindrically shaped in order to match the size of openings 34 of the first and second clamping members 22 and 24.

Figure 11:
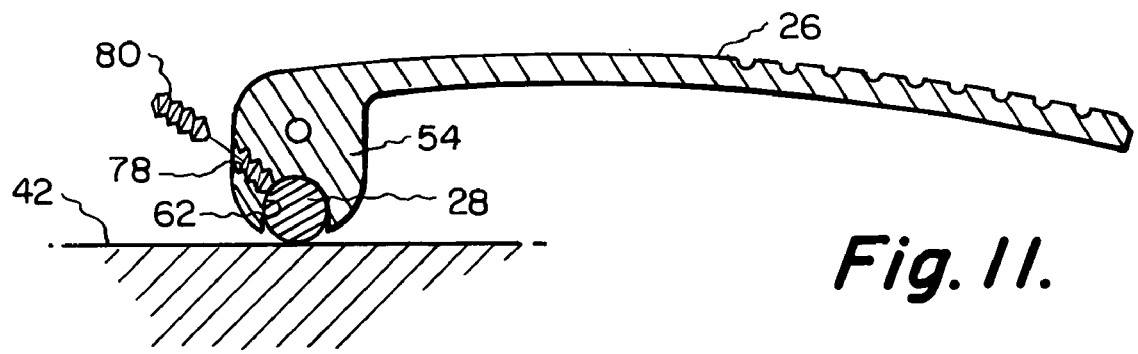
FIG. 11 is a side cross-sectional view showing one particular embodiment of a handle portion which forms a part of the locking mechanism of the present invention.

Each stationary jaw 54 is formed with a recess 62 which is designed to house the roller 28. The roller 28 associated with each individual stationary jaw 54 includes a circular channel 64 which extends into and around the circumference or periphery of each roller 28. The channel 64 on each of the rollers 28 receives the end of a pin 66 which extends through a bore 68 formed in each stationary jaw of the handle 26. The bore 68 extends into each recess 62. After the roller 28 is placed in the recess 62, the pin 66 is placed into the bore 68 to allow the end of the pin 66 to fit within the channel 64 formed on the roller 28, locking the roller 28 in place. The pin 66 can be permanently affixed into the bore using any one of a number of different techniques. In this manner, the roller 28 should remain fixed within the recess 62 in a tight fit with sufficient tolerance to still allow for the roller 28 to rotate on each stationary jaw. An alternative structure which can be used to adjust the amount of friction between the pin and the roller 28 is shown in FIG. 11 and will be discussed in greater detail below.

The washer 44 and bearing surface 42 are utilized to create the frictional engagement which allows the locking mechanism 20 to create the necessary clamping force to clamp the items together. As can be seen in FIGS. 2 and 5, the washer 44 may include an incline 70 which helps to both create the necessary clamping force while providing a surface which enhances the frictional contact to prevent slippage of the clamping force once the handle 26 is placed in the clamped position. This incline 70 is designed to contact the roller 28 as the roller 28 is moved into the final clamped position, as shown in FIG. 2, i.e., the incline 70 is at the end of the downward stroke when the handle 26 is moved down into the clamped position. The contact of the incline 70 with the roller 28 allows for increased frictional contact and actually helps to keep the handle 26 from being urged back into the unclamped position by the resiliency of the clamping members 22 and 24. As a result, the integrity of the locking mechanism is ensured since the counteracting force generated by the resiliency of the first and second clamping members will be overcome by the increased friction created between the bearing surface and the roller, the increased friction between the roller 28 and its housing recess 62 and the increased frictional contact between the pin 66 and the channel 64. Thus, once the locking mechanism is placed in the clamped position, there is little chance that the clamping members will loosen due to slippage or other factors. The incline 70 can be substantially linear in shape, or alternatively, curved in a shape similar to the shape of the outer periphery of the roller. When the incline is substantially the same shape as the roller, the amount of surface contact is increased which should increase the static friction that holds the roller in a locked position.

The washer 44 includes an opening 72 sized to receive the cross-sectional shape of the shaft 32 at its end 36. In this regard, the washer 44 will rotate with the handle 26 as the handle 26 is rotated 360° around the axis defined by the shaft 32. This particular configuration also allows each of the first and second clamping members 22 and 24 to rotate freely 360° relative to the axis defined by the shaft 32, as is shown in FIG. 4. As a result, the locking mechanism provides the user with multiple positions at which the handle can be rotated relative to the operating table and moved between clamped and unclamped positions. Thus, a retractor clamping assembly can be created which allows the surgical team to move the handle into any position around the shaft 32 while allowing the clamping members 22 and 24 to be moved to any desired angular position as well. The ease in moving the handle between clamped and unclamped position provides an easy and convenient clamping device to the surgical team.

Figure 10:
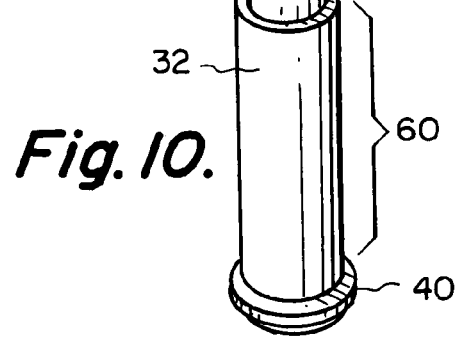
FIG. 10 is an exploded perspective view of the components which form the composite device depicted in FIG. 6.

Turning now to FIGS. 6-10, another embodiment of a locking mechanism 20 made in accordance with the present invention is disclosed. This particular locking mechanism is similar to the locking mechanism disclosed in FIGS. 1-5, except that the rollers 28 are attached to the stationary jaws 54 of the handle 26 in a different fashion. Referring specifically now to FIG. 10, the handle 26 is shown in which a housing slot 74 is formed into each of the stationary jaws 54 of the handle. These housing slots 74 are adapted to receive each of the rollers 28 and allow them to be rotatably mounted therein. A pin 76 fastens each of the rollers 28 within the housing slot 74 of each stationary jaw 54. It will be appreciated that alternative means for fastening the roller 28 into the slot 74 could be utilized, for example, a threaded pin or other fastening component. This particular embodiment of the locking assembly is different from the previously described embodiment; however, the manner of usage is exactly the same. In this regard, the handle 26 is moved in a downward fashion in order to create the actuating force which compresses the clamping members 22 and 24 as the roller contacts the bearing surface 42 of the washer 44. Again, an incline 70 located on the washer 44 helps to keep the handle in its clamped position and to avoid the possibility of slippage once placed in the clamped position. It should be appreciated to those skilled in the art that there are a number of alternative ways to rotatably attach each roller to the stationary jaws besides those described herein.

Referring now to FIG. 11, an alternative embodiment of the locking mechanism is shown. In this particular figure, the stationary jaw 56 of the handle 26 is shown including a threaded opening 78 adapted to receive a set screw 80 that acts as the holding pin described in the embodiments of FIGS. 1-5. The set screw 80 can be positioned, as needed, in frictional contact with the channel formed on the roller 28 in order to impart more or less frictional force on the roller. In this regard, if more frictional force is needed, the set screw can be tightened against the channel of the roller 28 to increase friction. As a result, an adjustable force can be imparted on the roller to change the characteristics of the roller as it moves between clamped and unclamped positions. It should be appreciated that the recess 62 formed on each stationary jaw 54 should be sufficiently large to prevent the roller 28 from being displaced from the jaw 54 as it is rotated. In this regard, when implementing the roller 28 in this particular embodiment, or the embodiment shown in FIGS. 1-5, the recess 62 should extend outward to contact a sufficiently large portion of the roller to prevent it from moving while still providing a sufficiently large area to permit the roller to contact the bearing surface.

Figure 12:
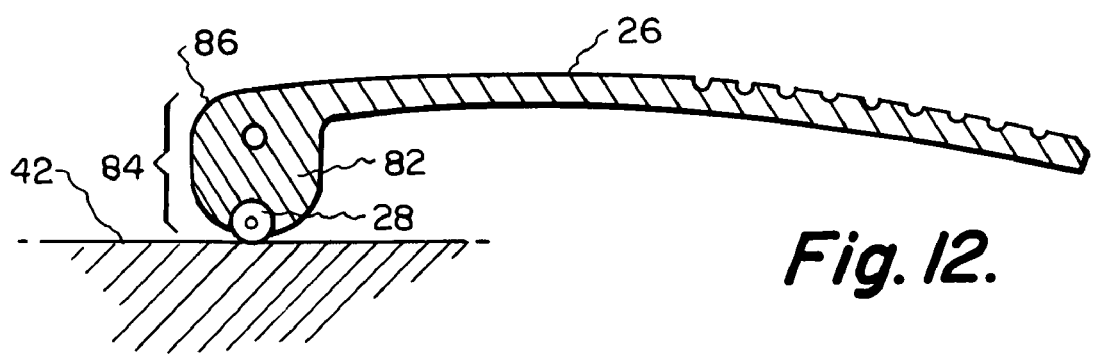
FIG. 12 is a side cross-sectional view of an embodiment of a locking mechanism made in accordance with the present invention associated with a camming member.

Referring now to FIG. 12, another embodiment of a locking mechanism made in accordance with the present invention is disclosed. In this particular embodiment, the handle 26 includes a camming member 82 used to create the actuating force that places the clamping devices in the clamped and unclamped position. Such camming members are well known in the art and are used to both actuate the device and maintain the device in the clamped position. Referring specifically to the camming member 82, a sliding cam surface 84 designated on the cam face 86 will initially contact the bearing surface in sliding engagement in order to start the application of the compressive force on the clamping devices. The sliding cam surface 84 should allow free sliding between surfaces when contact is made with the bearing surface, such as the bearing surface 42 on the washer. In this regard, it is desirous to have this area with a low coefficient of friction in order to create a free-sliding interface between the moving components. The cam face 86 further includes a frictional cam surface 88 designed to impart additional friction between the bearing surface and the cam face. This particular surface would be located on the cam face such that as the handle 26 is positioned into the clamped position, the frictional cam surface 88 lastly comes in contact with the bearing surface. As a result, the increased friction between the contacting surfaces is higher, which helps to lock the handle in the clamped position. This assures the user that once the handle is placed in the clamped position, there is little chance that the clamp can slip or become loosened due to frictional loss between the cam face and the bearing surface.

In the particular embodiment of FIG. 12, a roller 28 similar to the one described in the previous embodiments is used to form the frictional cam surface 88 on the cam face 86. In this regard, the attachment of the roller 28 to the camming member 82 can be similar to the embodiment shown in FIGS. 1-10, or by other fastening techniques. Accordingly, the frictional forces acting on the roller 28 help to prevent the handle 26 from moving once set in the clamped position. As with the other embodiments, a bearing surface 42 can include an incline, such as the inclined washer 44 shown in the previous embodiments, to enhance the locking of the camming member 82 with the bearing surface.

Figure 13:
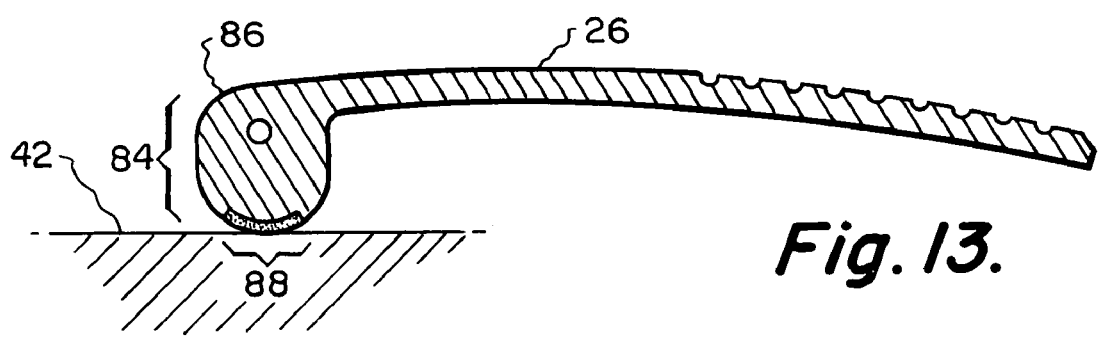
FIG. 13 is a side cross-sectional view of another embodiment of a locking mechanism associated with a camming member showing a sliding cam surface and frictional cam surface which form the composite cam face.
Figure 14:
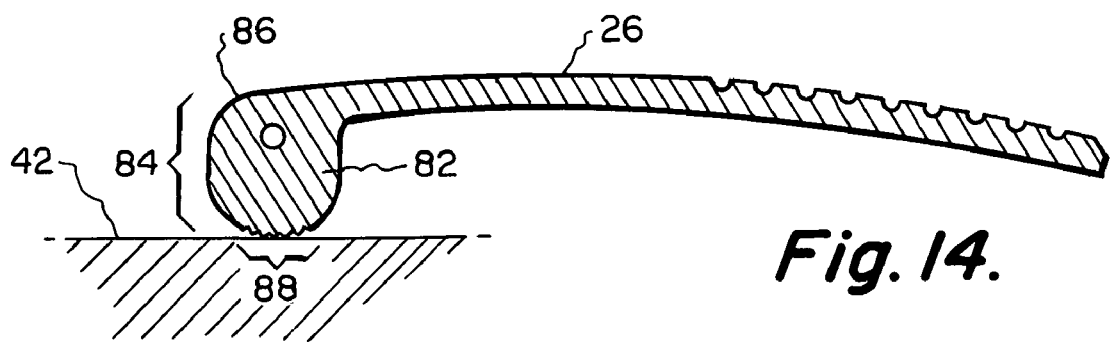
FIG. 14 is a side cross-sectional view of another embodiment of a locking mechanism associated with a camming member showing the sliding cam surface and an alternative frictional cam surface which form the composite cam face.
Figure 15:
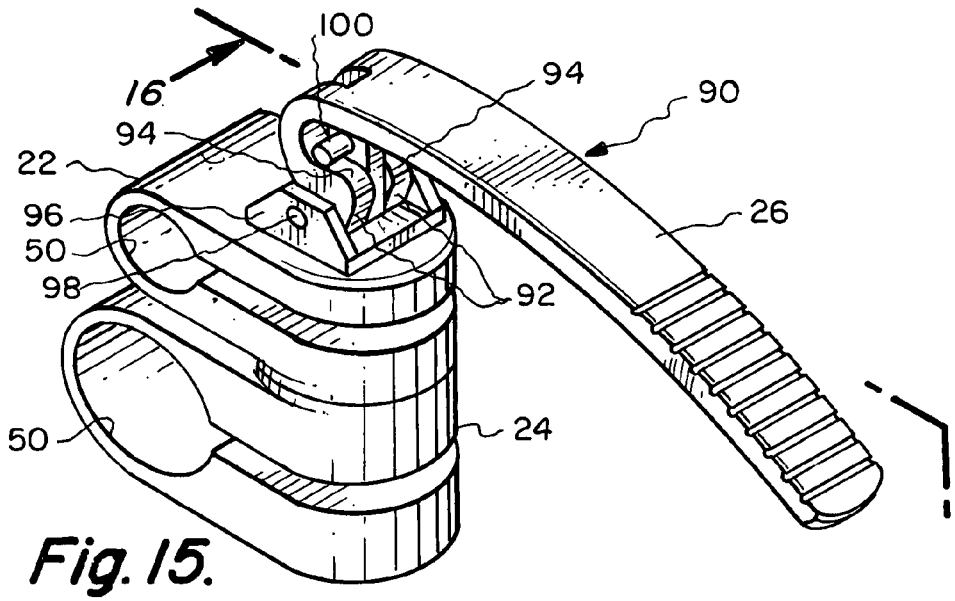
FIG. 15 is a perspective view of another particular embodiment of a locking mechanism made in accordance with the present invention coupled to a pair of conventional clamping devices.

Referring now to FIGS. 13 and 14, alternative designs for the camming member 82 are shown. Referring specifically to FIG. 13, the camming member 82 includes the sliding cam surface 84 which is located adjacent to the frictional cam surface 88 which is formed directly into the cam surface. For example, the frictional cam surface 88 can be made from a material which is different from the material forming the sliding cam surface 84 of the camming member 82. In this regard, a different material having a higher coefficient of friction can be utilized for the frictional cam surface 88, which again increases the frictional contact between the cam face and the bearing surface at the clamped position. There are numerous ways of attaching or forming the frictional cam surface 88 to the cam surface 86 including, for example, bonding a different material onto the cam face 86 itself. It will apparent to those skilled in the art that still other ways of fashioning the sliding cam surface 84 with respect to the frictional cam surface 88 can be achieved. In FIG. 14, the frictional cam surface 88 is shown as a surface treated region. Suitable surface treatment include the scoring the cam face to produce a region having a higher frictional coefficient once in contact with the bearing surface. Still other techniques which can create a roughened surface in this particular region of the cam member can be utilized in order to increase the frictional contact between sliding components.

Figure 16:
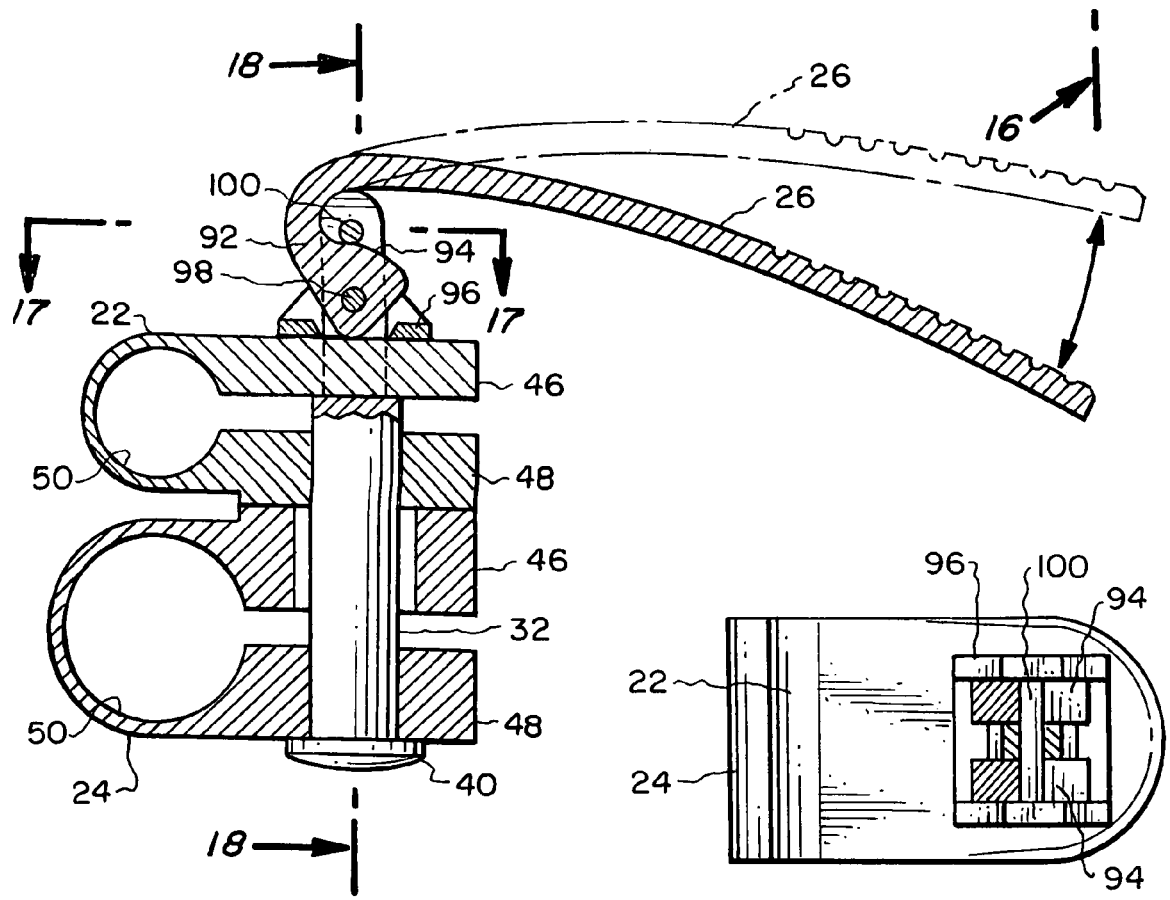
FIG. 16 is a cross-sectional side view of the composite device depicted in FIG. 15 taken along lines 16-16 which shows the contact between the camming member and the sliding pin of the locking mechanism.
Figure 17:
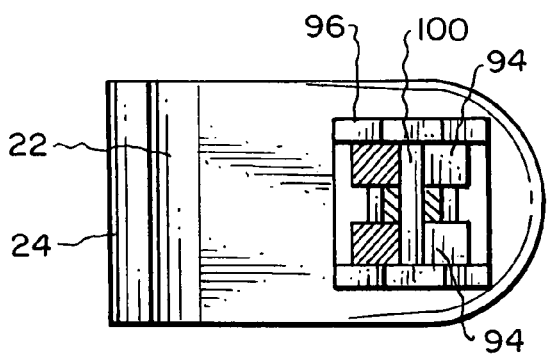
FIG. 17 is a partial cross-sectional view of the composite device depicted in FIG. 15 taken along lines 17-17 which shows the camming portion of the handle of this particular embodiment of the locking mechanism.
Figures 18, 19:
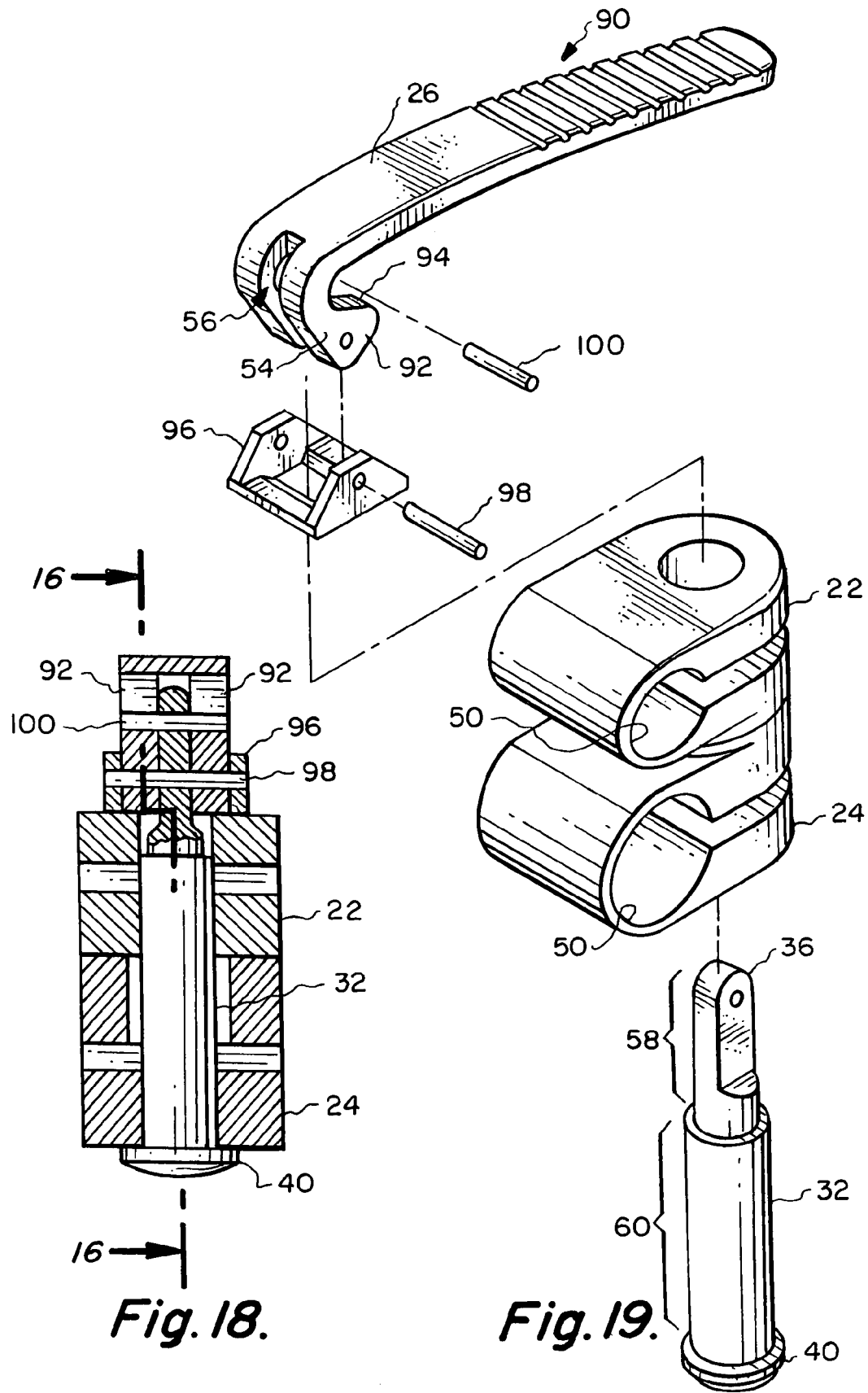
FIG. 18 is a cross-sectional side view of the composite device depicted in FIG. 15 taken along lines 18-18.
FIG. 19 is an exploded perspective view of the components which form the composite device depicted in FIG. 15.

Referring now to FIG. 19, another embodiment of a locking mechanism 90 made in accordance with the present invention is shown. This particular embodiment includes the handle portion 26, a pair of stationary jaws 92 which have a camming surface 94 associated with each jaw. Each of the stationary jaws 92 is pivotally attached to a support frame 96 which includes a pivot pin 98 that allows the handle to be pivotally attached thereto. The end of the shaft 32 includes a sliding pin 100 which is in sliding contact with the camming surface 94 formed on each stationary jaw 92. As can best be seen in FIG. 16, as the handle 26 is moved in an upward or downward position, the sliding pin 100 contacts the camming surface 94 and moves in either an upward or a downward fashion depending upon the position of the handle. In this fashion, the actuating or compressive force can be applied to the clamping members 22 and 24 in the same fashion as in the other locking mechanisms of the present invention. In this particular embodiment, however, the clamping force is obtained by moving the handle from a lower position to a higher position, as is shown in FIG. 16. In this regard, as the handle is lifted up, the sliding pin 100 follows the contour of the camming surface 94 and is raised, causing the support frame 96 to contact the first clamping member 22 and to create the compressive force on the clamping members. Accordingly, this locking mechanism 90 will maintain the clamping members 22 and 24 in a clamped position and can be quickly and easily realigned or repositioned by simply moving the handle 26 in an upward stroke.

The locking mechanism can be made utilizing suitable biocompatible materials such as stainless steel. The roller used in accordance with the disclosed embodiments can be made either of stainless steel or of another biocompatible material which is suitable for use. The washer which provides the bearing surface can also be made from suitable materials such as stainless steel or brass alloys and the like which are biocompatible. Preferably, the materials which are selected should be susceptible to sterilization using such methods as autoclaving.

While the invention has been illustrated and described herein, in terms of its use with clamping devices, it will be apparent to those skilled in the art that the device can take on a number of different forms and a number of different applications, both medical and non-medical. Other modifications and improvements may be made without departing from the scope of the invention.

What is claimed is:

1. A clamping apparatus, comprising:
    a roller locking mechanism including a handle and a roller rotatably attached to the handle;
    a clamping assembly including a first clamping member; and
    a shaft member for coupling the roller locking mechanism with the first clamping member, wherein the handle includes a stationary jaw having a recess formed therein for receiving the roller and the roller has a channel disposed into the peripheral edge of the roller, the stationary jaw including an opening which extends to the recess formed therein and a pin adapted to fit within the opening in the stationary jaw and having an end which is engagable within the channel formed on the roller to maintain the roller rotatably mounted within the recess, and a second stationary jaw having a recess formed therein for receiving a second roller, the second roller having a channel disposed into the peripheral edge of the second roller, the second stationary jaw including an opening which extends to the recess formed therein and a pin adapted to fit within the opening in the second stationary jaw and having an end which is engagable within the channel formed on the second roller to maintain the second roller rotatably mounted within the recess.

2. The clamping apparatus of claim 1, wherein the clamping assembly further includes a second clamping member and the shaft member couples the second clamping member with the roller locking mechanism and first clamping member.

3. The clamping apparatus of claim 2, wherein the roller locking mechanism, first clamping member and second clamping member are independently rotatable with respect to each other.

4. The clamping apparatus of claim 1, wherein the opening in at least one of the stationary jaws is threaded and the pin is threaded and selectively movable in the opening to vary the amount of frictional contact that the end of the pin makes with the channel formed on the roller.

5. The clamping apparatus of claim 1, further including:
    a bearing surface which engages the roller, the bearing surface including an incline adapted to place the roller in a locked position.

6. The clamping apparatus of claim 5, wherein the bearing surface is located on a washer, the washer being in contact with the first clamping member.

7. The clamping apparatus of claim 5, wherein the handle is pivotally attached to the shaft member.

8. The clamping apparatus of claim 1, wherein the opening in at least one of the stationary jaws is threaded and the pin is threaded to be screwed into the threaded opening.

* * * * *